Figure 2:
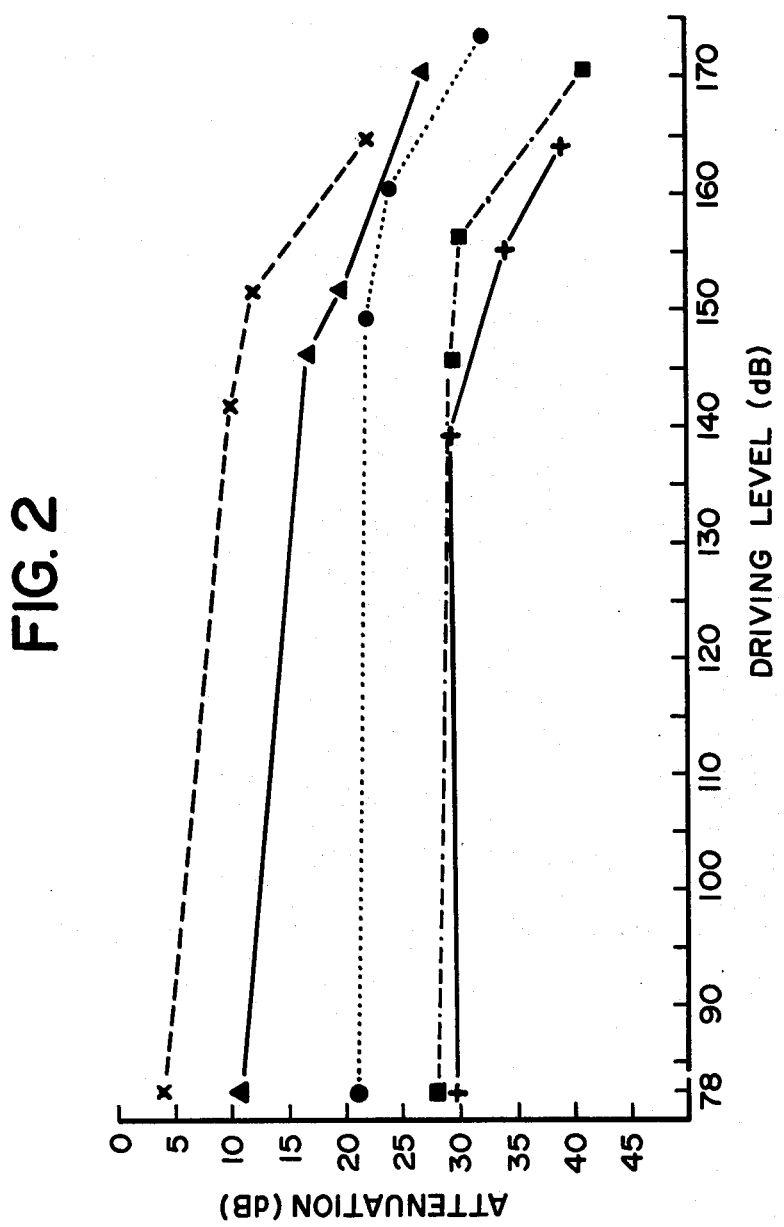

United States Patent [19]

Stallings

[11] Patent Number: 4,465,159
[45] Date of Patent: Aug. 14, 1984

[54] NONLINEAR EAR PROTECTING DEVICE

[75] Inventor: John P. Stallings, Indianapolis, Ind.

[73] Assignee: Cabot Corporation, Kokomo, Ind.

[21] Appl. No.: 474,617

[22] Filed: Mar. 11, 1983

[51] Int. Cl.³ ............................................. N04R 25/00
[52] U.S. Cl. .................................. 181/129; 179/182 R
[58] Field of Search ................................ 181/129, 126;
179/107 R, 182 A, 182 R, 180; 128/152, 151;
2/209

[56] References Cited

U.S. PATENT DOCUMENTS

| | | | |
|---|---|---|---|
| 1,909,856 | 5/1933 | Dolder | 2/209 X |
| 2,441,866 | 5/1948 | Cantor | 128/152 |
| 3,454,962 | 7/1969 | Hind | 2/209 X |
| 3,454,964 | 7/1969 | Brinkhoff | 179/182 R X |
| 3,588,914 | 6/1971 | Ihnat, Jr. | 2/209 X |
| 3,637,040 | 1/1972 | Gorman | 179/182 R X |
| 3,644,939 | 2/1972 | Beguin | 2/209 |
| 3,661,225 | 5/1972 | Anderson | 128/152 X |
| 3,728,741 | 4/1973 | Lepor | 2/209 |
| 3,823,713 | 7/1974 | Shah | 2/209 X |
| 3,908,200 | 9/1975 | Lundin | 179/182 R X |
| 4,094,303 | 6/1978 | Johnston | 128/151 X |
| 4,174,155 | 11/1979 | Herman | 181/126 X |

OTHER PUBLICATIONS

M. R. Forrest, Laboratory Dev. of an Amplitude-Sensitive Ear Plug, Oct. 1969.
M. R. Forrest, R. R. A. Coles, Problems of Communication and Ear Protection in the Royal Marines, (1970).
J. Zwislocki, New Types of Ear Protectors, (1952).
A. M. Martin, Dependence of Acoustic Attenuation of Hearing Protectors on Incident Sound Level, (1979).

Primary Examiner—L. T. Hix
Assistant Examiner—Brian W. Brown
Attorney, Agent, or Firm—Jack Schuman; Joseph J. Phillips; Robert F. Dropkin

[57] ABSTRACT

An ear protecting device for protecting a wearer from annoying and/or damaging noise levels. The device is comprised of a connecting member and a pair of muffs suitable for covering a wearer's ears. The muffs are suspended from opposite portions of the connecting member. The muffs are each comprised of a cup and an earseal cushion. The muffs are characterized by greater attenuation in high intensity environments than in low intensity environments. Each muff has a cup which is at least partially porous. Each muff has a specific airflow resistance of from between 3,000 and 105,000 SI rayls. At least one porous portion of each cup defines a tortuous path. The mean pore size of this porous portion is at least 160 micrometers.

11 Claims, 11 Drawing Figures

NONLINEAR EAR PROTECTING DEVICE

The present invention relates to an ear protecting device.

Numerous ear protecting devices have been developed for protecting a wearer from annoying and/or damaging noise levels. One class of such devices, generally known as earmuffs, is comprised of a connecting member and a pair of muffs suitable for covering a wearer's ears. The muffs are suspended from opposite portions of the connecting member.

Earmuffs have been, and are, a significant factor in the hearing protection market. Their use, as a fraction of the total ear protecting device market, has however been declining despite the fact that the number of earmuff manufacturers has increased. This is, in part, due to the fact that they screen out speech and other types of meaningful sound. This can be detrimental.

The present invention overcomes the heretofore referred to shortcoming of earmuffs by providing an earmuff which permits the user to comfortably listen to speech and other types of meaningful sound in a low intensity environment, yet one which achieves useful attenuation in a high intensity environment. The present invention provides a passive nonlinear (amplitude dependent) hearing protector characterized by greater attentuation in high intensity environments than in low intensity environments.

The desirable combination of properties of the muff of the present invention is achieved by making the muff porous and by controlling the nature of the porosity. The muff is characterized by pores of certain minimum size, which define a tortuous path between opposite sides thereof.

Inter-aural nonlinear hearing protectors are described in the following references:
1. Forrest, M. R.—Laboratory Development of an Amplitude-Sensitive Ear Plug—Report He S133, RNPRC, MRC of Great Britain, 1969;
2. Forrest, M. R. and Coles, R. R. A.—Problems of Communication and Ear Protection in the Royal Marines, Journal of Royal Naval Medical Service, 1970, 56, 162-169; and
3. Zwislocki, J.—New Types of Ear Protectors, Journal of the Acoustical Society of America, 1952, 24, 762-764.

The hearing protectors of these references are essentially earplugs with a tiny orifice therethrough.

The orifice in the earplugs of the hereinabove cited references is considerably different from the porous muff of the present invention. This will become clear from the forthcoming description thereof.

The porous muff of the present invention is also considerably different from the open or porous materials of the ear protecting devices disclosed in the following U.S. Pat. Nos.: 1,909,856; 2,441,866; 3,454,962; 3,588,914; 3,637,040; 3,644,939; 3,661,225; 3,728,741; 3,823,713; 4,094,303; and 4,174,155. None of them disclose a nonlinear ear protecting device such as that of the present invention.

A. M. Martin (Dependence of Acoustic Attenuation of Hearing Protectors on Incident Sound Level, British Journal of Industrial Medicine, 1979, 36, 1-14) tested the ear protecting device of U.S. Pat. No. 3,637,040. He found no significant difference (at the 0.05 level of confidence) in attenuation in high and low intensity environments.

It is accordingly an object of the present invention to provide an ear protecting device which permits the user to comfortably listen to speech and other types of meaningful sound in a low intensity environment while providing meaningful attenuation in a high intensity environment.

Figure 1:
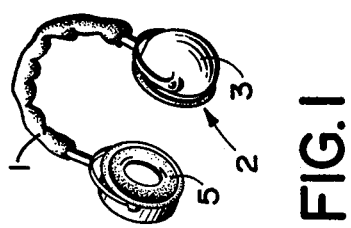

The foregoing and other objects of the invention will become apparent from the following detailed description taken in connection with the accompanying drawings which form a part of this specification, and in which:

FIG. 1 is a perspective view of the structure for a typical hearing protector device within the present invention; and FIGS. 2 through 11 are plots of attenuation versus the driving level of a source of sound at varying frequencies.

The present invention provides an ear protecting device which permits the user to comfortably listen to speech and other types of meaningful sound in a low intensity environment while providing meaningful attenuation in a high intensity environment. The device is comprised of a connecting member and a pair of muffs suitable for covering a wearer's ears. The muffs are suspended from opposite portions of the connecting member. The connecting member can be a band, such as a headband, or a helmet with auxiliary hardware, or any other means which are or which may become known to those skilled in the art. The muffs have a specific airflow resistance of between 3,000 and 105,000 SI rayls. The muffs are comprised of a cup and an earseal cushion. Each of the cups are at least partially porous. At least one porous portion of each of the cups defines a tortuous path between opposite sides thereof. At least one porous portion of each of the cups has a mean pore size of at least 160 micrometers.

The desirable combination of properties attributable to the muffs of the present invention is achieved by making the cup of each muff porous, and by controlling the nature of the porosity. Each cup has a porous portion which, as stated hereinabove, defines a tortuous path between opposite sides thereof. The surface area of this porous portion is generally at least 1 square centimeter. The mean pore size of the pores of this porous portion is at least 160 micrometers, and generally at least 190 micrometers. A minimum pore size is imposed as acoustic radiation resistance increases with increasing pore size. Acoustic radiation resistance, defined in ohms, is an accurate description of the ability of an orifice to impede a sound wave. Within the effective area of the pores, a further increase in radiation resistance is attributable to the tortuous path. Mean pore size is usually in the range of from 190 to 300 micrometers.

The muffs of the present invention are preferably tuned to a frequency of from 250 to 1000 Hz as nonlinear attenuation is believed to be superior at the resonant frequency of the system and as attenuation with respect to high intensity noises such as gunfire and jet aircraft is most prominent in this frequency range. Tuning is accomplished by controlling the size of the pores and/or the length of the pores and/or the enclosed volume of the pores.

The muffs of the present invention have a specific airflow resistance of between 3,000 and 105,000 SI rayls. Attenuation increases as the specific airflow resistance increases. A specific airflow resistance of 3,000 SI rayls is needed for minimum attenuation. The specific airflow resistance is usually at least 10,000 SI rayls. The specific airflow resistance is kept below 105,000 SI rayls as it is difficult to achieve the nonlinear affect of the present invention with higher specific airflow resistances. The present invention is characterized by an attenuation which is at least 3 dB and generally at least 5 dB greater at an intensity of 170 dB and a frequency of 500 Hz than at an intensity of 78 dB and a frequency of 500 Hz. Differences in excess of 10 dB have been achieved.

The structure for a typical hearing protector device within the present invention is shown in FIG. 1. It is comprised of headband 1 and muffs 2. Muffs 2 are comprised of cups 3 and earseal cushions 5. The cups can be partially or entirely porous. They can be entirely porous cups with coated nonporous portions, porous cups which have been precompressed to alter their porosity or nonporous cups with a porous insert. Porosity can, as one might expect, be attained using any process and/or material which will provide the cup with a porous portion as discussed hereinabove. Exemplary materials include polypropylene, ultra high molecular weight polyethylene resins, glass frits, ceramics and metals. Polypropylene is presently preferred. Ultra high molecular weight polyethylene resins have a weight average molecular weight of at least $3.5 \times 10^6$ as measured by the solution viscosity method.

Additional advantages are attributable to the porosity of the muff of the present invention. The porous portion of the muff allows for moisture transmission and for the escape of water vapor caused by perspiration. The porous portion of the muff also allows the muff to compensate for rapid changes in pressure which occur on aircraft and submarines.

The following examples are illustrative of several aspects of the invention.

EXAMPLE I

The cup portion of the muffs of a commercially available ear protecting device were fitted with a polypropylene porous insert. The insert was 2.54 centimeters in diameter and 0.625 centimeters thick. The polypropylene had a nominal pore size of 250 micrometers. The path defined by the pores was tortuous. The resonant frequency of the device was from 250 to 500 Hz.

The ear protecting device was tested for specific airflow resistance in accordance with the procedure set forth in ASTM C-522-80. It was determined to be $1.63 \times 10^4$ SI rayls, based on the total internal surface area of the muff.

Figure 3:
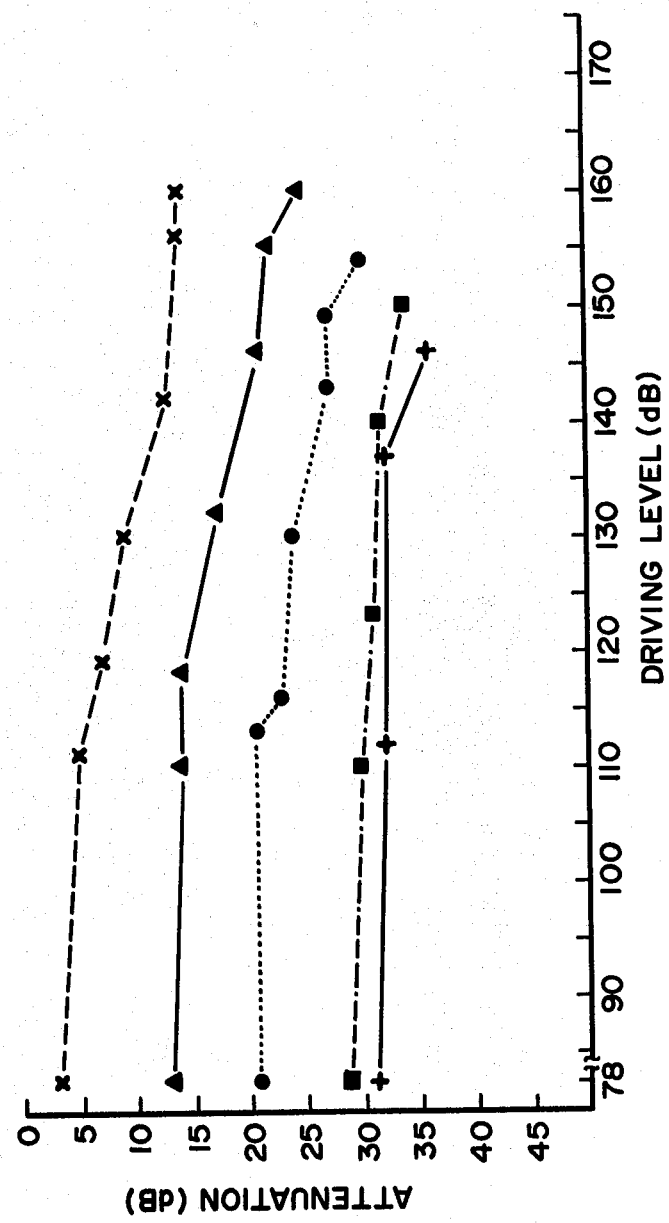

A graphical presentation of attenuation versus the driving level of a source of sound is seen in FIGS. 2 and 3. Gunfire was used to obtain all the data points, with the exception of the 78 dB data points, for FIG. 2. High level steady state noise was used to obtain all the data points, with the exception of the 78 dB data points, for FIG. 3. Low level steady state noise was used to obtain the 78 dB data points. The data points are identified as follows:

1. "×"—250 Hz
2. "▲"—500 Hz
3. "●"—1000 Hz
4. "■"—2000 Hz
5. "+"—4000 Hz

Attenuation was determined in accordance with the ANSI-S3.19 blockhead attenuation test using silicone flesh. Although impulses from gunfire are not included within the ANSI specification, all other procedures thereof were followed.

As seen in FIGS. 2 and 3, the device of the example is nonlinear. The device of this example is characterized by greater attenuation in high intensity environments than in low intensity environments. Nonlinear attenuation appears to start to take place in the 110 to 120 dB driving level range.

The device of this example is in accordance with the present invention.

EXAMPLE II

Figure 4:
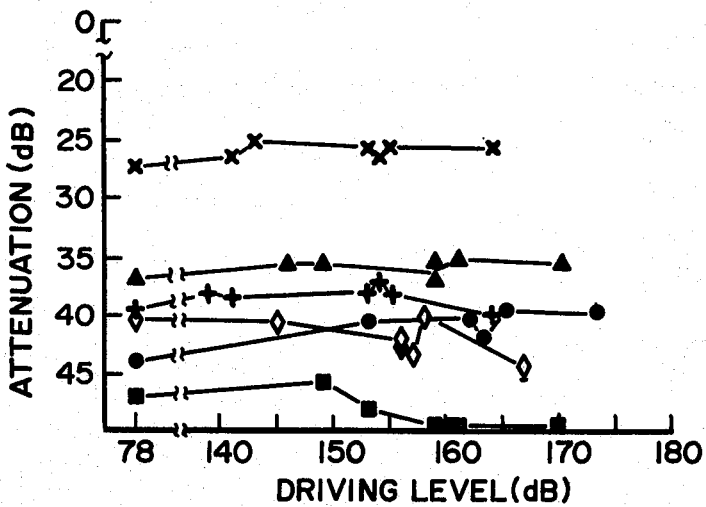

A graphical presentation of attenuation versus the driving level of a source of sound is seen in FIG. 4 for another commercially available ear protecting device. The cups of this device were not fitted with porous inserts. High level steady state noise was used to obtain the data points with the exception of the 78 dB data points. Low level steady state noise was used to obtain the 78 dB data points. The data points are identified in the same manner as in Example I, with the following addition: "△"—3,150 Hz. Attenuation was determined in accordance with the ANSI-S3.19 blockhead attenuation test using silicone flesh.

As seen in FIG. 4, the device of this example is linear. There is no significant difference in attenuation across the driving levels. The device of this example is not in accordance with the present invention.

EXAMPLE III

The ear protecting device of Example II was modified. A single, ¼ inch diameter hole was drilled into each cup. The device was tuned to 250 Hz.

Figure 5:
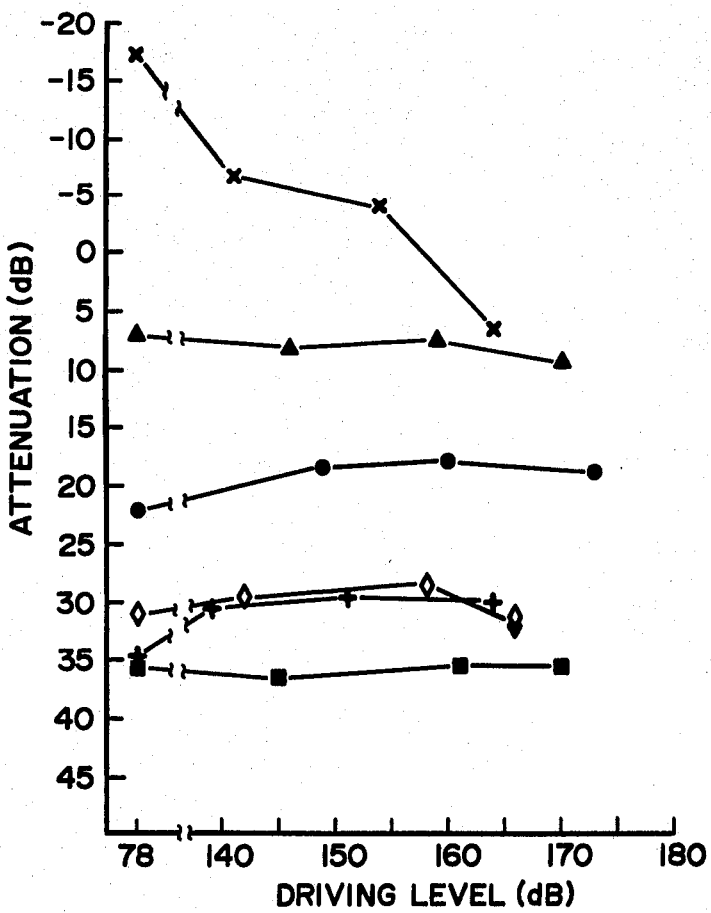

A graphical presentation of attenuation versus the driving level of a source of sound, for the modified device of this example, is seen in FIG. 5. High level steady state noise was used to obtain the data points with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

The device of this example is unsatisfactory. The 250 Hz band, the only band to show a substantial nonlinear attenuation, is characterized by an insertion gain at a driving level of 155 dB. Such an insertion gain would leave the user particularly vulnerable to a dosage of severe noise.

The device of this example is not in accordance with the present invention. The ¼ inch diameter hole does not define a tortuous path between opposite sides of the cup.

EXAMPLE IV

The ear protecting device of Example II was modified. Twenty, 0.5 mm diameter holes were drilled in each cup. The device was tuned to 250 Hz.

Figure 6:
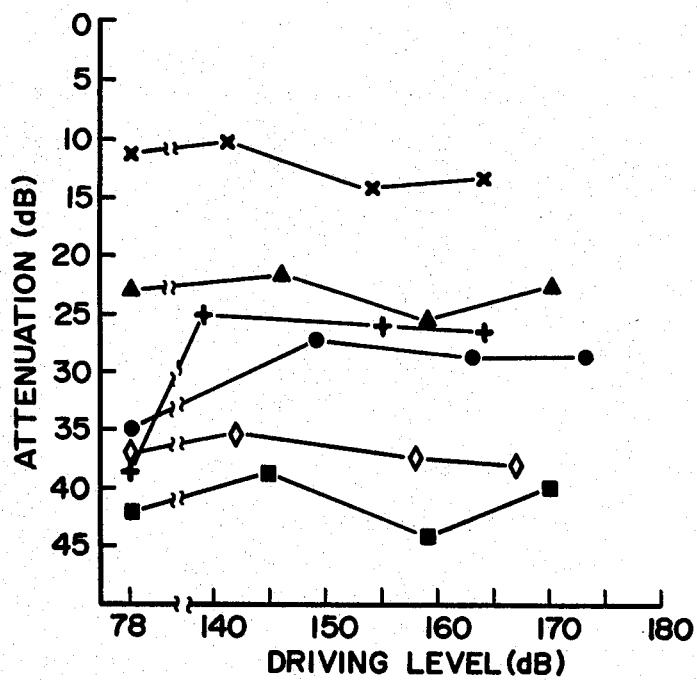

A graphical presentation of attenuation versus the driving level of a source of sound, for the modified device of this example, is seen in FIG. 6. High level steady state noise was used to obtain the data points with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

As seen in FIG. 6, the device of this example is linear. There is no significant difference in attenuation across the driving levels.

The device of this example is not in accordance with the present invention. The 0.5 mm diameter holes do not define a tortuous path between opposite sides of the cup.

EXAMPLE V

The ear protecting device of Example II was modified. It was fitted with a polypropylene porous insert. The insert was 0.495 inch in diameter and 0.19 inch thick. The polypropylene had a minimal pore size of 120 micrometers. The path defined by the pores was tortuous. The device was tuned to 250 Hz.

Figure 7:
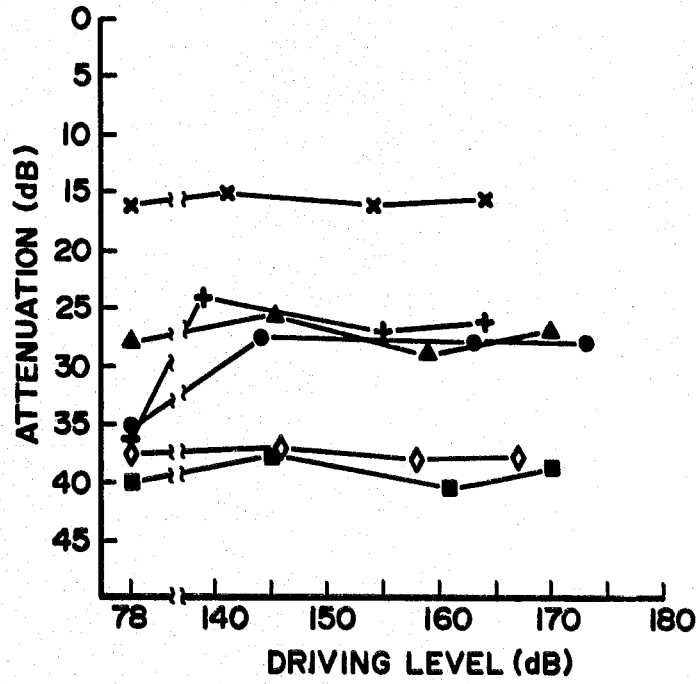

A graphical presentation of attenuation versus the driving level of a source of sound, for the modified device of this example, is seen in FIG. 7. High level steady state noise was used to obtain the data points, with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

As seen in FIG. 7, the device of this example is linear. There is no significant difference in attenuation across the driving levels.

The device of this example is not in accordance with the present invention. A nominal pore size of 120 micrometers is believed to be too small to create a sufficient nonlinear radiation resistance. The present invention calls for a mean pore size of at least 160 micrometers.

EXAMPLE VI

The ear protecting device of Example II was modified. It was fitted with a polypropylene porous insert. The insert was 0.498 inch in diameter and 0.212 inch thick. The polypropylene had a nominal pore size of 200 micrometers. The path defined by the pores was tortuous. The device was tuned to 250 Hz.

The ear protecting device of this example was tested for specific airflow resistance in accordance with the procedure set forth in ASTM C-522-80. It was determined to be $1.01 \times 10^5$ SI rayls, based on the total internal surface area of the muff.

Figure 8:
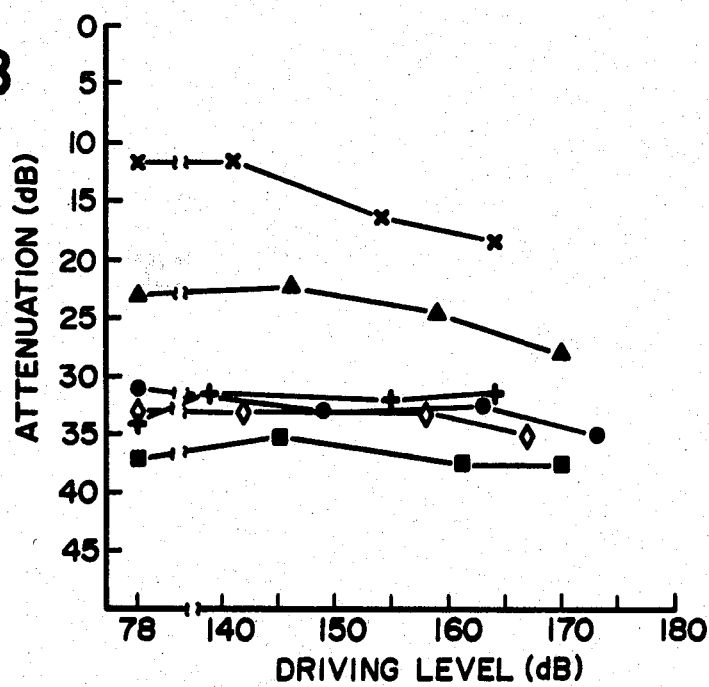

A graphical presentation of attenuation versus the driving level of a source of sound, for the modified device of this example, is seen in FIG. 8. High level steady state noise was used to obtain the data points, with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

As seen in FIG. 8, the device of this example is nonlinear. The 250 Hz, 500 Hz and 1000 Hz bands are characterized by greater attenuation in high intensity environments than in low intensity environments.

The device of this example is in accordance with the present invention.

EXAMPLE VII

The ear protecting device of Example II was modified. It was fitted with a polypropylene porous insert. The insert was 0.480 inch in diameter and 0.141 inch thick. The polypropylene had a nominal pore size of 250 micrometers. The path defined by the pores was tortuous. The device was tuned to 250 Hz.

The ear protecting device of this example was tested for specific airflow resistance in accordance with the procedure set forth in ASTM C-522-80. It was determined to be $1.33 \times 10^4$ SI rayls, based on the total internal surface area of the muff.

Figure 9:
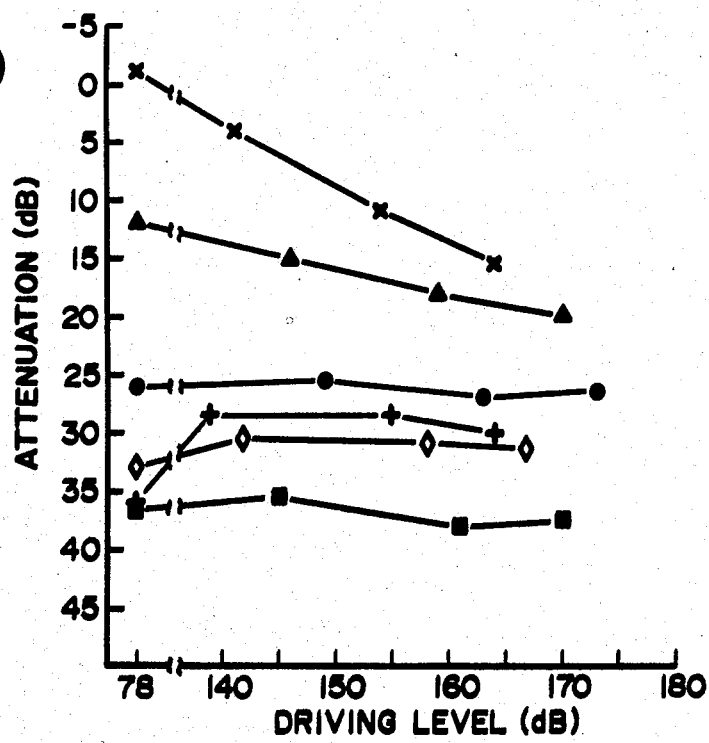

A graphical presentation of attenuation versus the driving level of a source of sound for the modified device of this example, is seen in FIG. 9. High level steady state noise was used to obtain the data points, with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

As seen in FIG. 9, the device of this example is nonlinear. The 250 Hz and 500 Hz bands are characterized by greater attenuation in high intensity environments than in low intensity environments.

The device of this example is in accordance with the present invention.

EXAMPLE VIII

The ear protecting device of Example II was modified. It was fitted with a polypropylene porous insert. The insert was 1.005 inch in diameter and 0.212 inch thick. The polypropylene had a nominal pore size of 200 micrometers. The path defined by the pores was tortuous. The device was tuned to 500 Hz.

The ear protecting device of this example was tested for specific airflow resistance in accordance with the procedure set forth in ASTM C-522-80. It was determined to be $1.4 \times 10^4$, SI rayls based on the total internal surface area of the muff.

Figure 10:
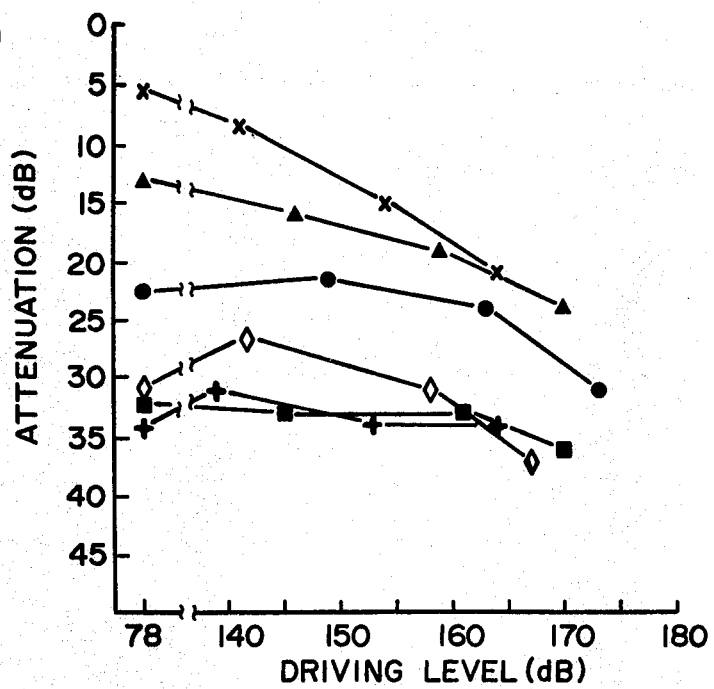

A graphical presentation of attenuation versus the driving level of a source of sound for the modified device of this example, is seen in FIG. 10. High level steady state noise was used to obtain the data points, with the exception of the 78 dB data points. Low level steady state noise was used to obtain the 78 dB data points. The data points are identified in the same manner as in the preceding examples. Attenuation was determined in accordance with the ANSI-S3.19 blockhead attenuation test using silicone flesh.

As seen in FIG. 10, the device of this example is nonlinear. The 250 Hz, 500 Hz and 1000 Hz bands are characterized by greater attenuation in high intensity environments than in low intensity environments.

The device of this example is in accordance with the present invention.

EXAMPLE IX

The ear protecting device of Example II was modified. It was fitted with a polypropylene porous insert. The insert was 1.025 inch in diameter and 0.275 inch thick. The polypropylene had a nominal pore size of 250 micrometers. The path defined by the pores are tortuous. The device was tuned to 500 Hz.

The ear protecting device of this example was tested for specific airflow resistance in accordance with the procedure set forth in ASTM C-522-80. It was determined to be $3.06 \times 10^3$ SI rayls, based on the total internal surface area of the muff.

Figure 11:
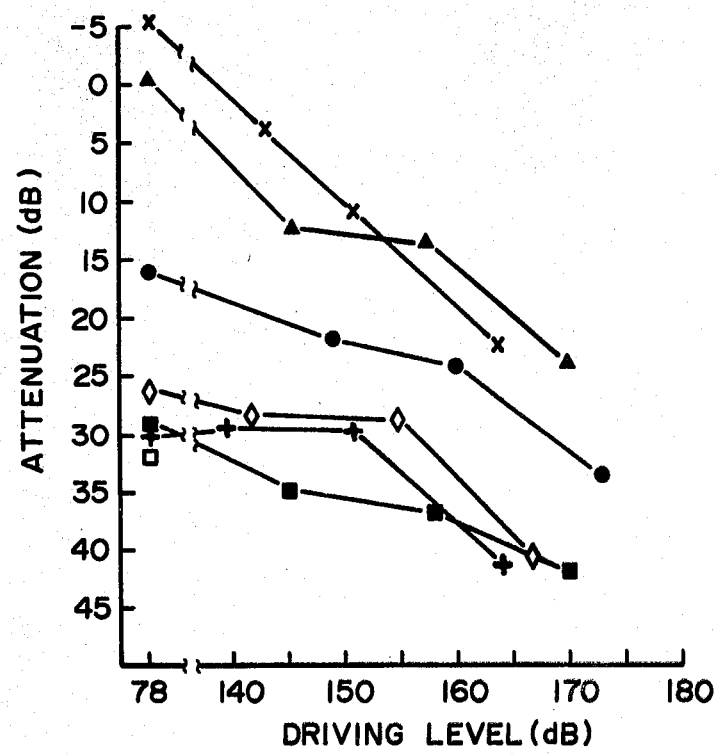

A graphical presentation of attenuation versus the driving level of a source of sound for the modified device of this example, is seen in FIG. 11. High level steady state noise was used to obtain the data points, with the exception of the 78 dB data points. Low level steady state noise was used to obtain the 78 dB data points. The data points are identified in the same nammer as in the preceding examples. Attenuation was determined in accordance with the ANSI-S3.19 blockhead attenuation test using silicone flesh.

As seen in FIG. 11, the device of this example is nonlinear. The 250 Hz, 500 Hz and 1000 Hz bands are characterized by greater attenuation in high intensity environments than in low intensity environments.

The device of this example is in accordance with the present invention.

It will be apparent to those skilled in the art that the novel principles of the invention disclosed herein in connection with specific examples thereof will support various other modifications and applications of the same. It is accordingly desired that in construing the breadth of the appended claims they shall not be limited to the specific examples of the invention described herein.

I claim:

1. In an ear protecting device for protecting a wearer from annoying and/or damaging noise levels, which device is comprised of: a connecting member and a pair of muffs suitable for covering a wearer's ears, said muffs being suspended from opposite portions of the connecting member, said muffs each being comprised of a cup and an earseal cushion: the improvement comprising; muffs which are characterized by greater attenuation in high intensity environments than in a low intensity environments, each said muff having a cup which is at least partially porous, each said muff having a specific airflow resistance of between 3,000 and 105,000 SI rayls, at least one porous portion of each said cup defining a tortuous path, said at least one porous portion of each said cup having a mean pore size of at least 160 micrometers.

2. An ear protecting device according to claim 1, wherein the attenuation at an intensity of 170 dB and a frequency of 500 Hz is at least 3 dB greater than the attenuation at an intensity of 78 dB and a frequency of 500 Hz.

3. An ear protecting device according to claim 1, wherein said specific airflow resistance is at least 10,000 SI rayls.

4. An ear protecting device according to claim 1, wherein said mean pore size is at least 190 micrometers.

5. An ear protecting device according to claim 4, wherein said mean pore size is between 190 and 300 micrometers.

6. An ear protecting device according to claim 2, wherein the attenuation at an intensity of 170 dB and a frequency of 500 Hz is at least 5 dB greater than the attenuation at an intensity of 78 dB and a frequency of 500 Hz.

7. An ear protecting device according to claim 1, wherein the surface area of said porous portion of each said cup is at least 1 square centimeter.

8. An ear protecting device according to claim 1, wherein each of said cups is formed from a nonporous material and wherein each of said cups has a porous insert.

9. An ear protecting device according to claim 8, wherein said porous insert is polypropylene.

10. An ear protecting device according to claim 1, wherein the device is tuned to a frequency of from 250 to 1000 Hz.

11. An ear protecting device according to claim 1, wherein the attenuation at an intensity of 170 dB and a frequency of 500 Hz is at least 10 dB greater than the attenuation at an intensity of 78 dB and a frequency of 500 Hz.

* * * * *